United States Patent [19]

Iwatschenko

[11] Patent Number: 4,834,725
[45] Date of Patent: May 30, 1989

[54] CATHETER FOR PERCUTANEOUS GASTROSTOMY

[75] Inventor: Peter Iwatschenko, Neunkirchen, Fed. Rep. of Germany

[73] Assignee: 501 Pfrimmer-Viggo GmbH & Co., Fed. Rep. of Germany

[21] Appl. No.: 24,143

[22] Filed: Mar. 10, 1987

[30] Foreign Application Priority Data

Mar. 27, 1986 [DE] Fed. Rep. of Germany ....... 3610419

[51] Int. Cl.⁴ ............................................. A61M 25/00
[52] U.S. Cl. ..................................... 604/281; 604/764
[58] Field of Search ...................... 604/281, 264–265, 604/275, 287, 327, 328, 280

[56] References Cited

U.S. PATENT DOCUMENTS

| 2,452,813 | 11/1948 | Wade | 604/328 |
|---|---|---|---|
| 2,603,217 | 7/1952 | McShirley | 604/265 |
| 3,155,097 | 11/1964 | Barron | 604/265 |
| 3,680,562 | 8/1972 | Wittes et al. | 604/281 |
| 3,736,939 | 6/1973 | Taylor | 604/265 |
| 3,860,006 | 1/1975 | Patel | 604/281 |
| 4,182,342 | 1/1980 | Smith | 604/265 |
| 4,243,030 | 1/1981 | Lynch et al. | 604/264 |
| 4,531,933 | 7/1985 | Norton et al. | 604/281 |
| 4,596,564 | 6/1986 | Spetzler et al. | 604/281 |
| 4,668,225 | 5/1987 | Russo et al. | 604/264 |
| 4,738,667 | 4/1988 | Galloway | 604/281 |

FOREIGN PATENT DOCUMENTS

| 3214905 | 12/1982 | Fed. Rep. of Germany . | |
|---|---|---|---|
| 1263097 | 4/1961 | France | 604/281 |
| 1249957 | 10/1971 | United Kingdom | 604/281 |

OTHER PUBLICATIONS

Article by M. Keymling, M. Schroeder, W. Worner entitled "Experience with the Percutaneous Endoscopically Controlled Gastrostomy (PEG)", published 1985, 36: 1297–1301.

Primary Examiner—C. Fred Rosenbaum
Assistant Examiner—Kathleen A. Daley
Attorney, Agent, or Firm—Brumbaugh, Graves, Donohue & Raymond

[57] ABSTRACT

A catheter of plastic material for percutaneous gastrostomy is introduced directly through the abdominal wall into the gastric lumen (16) where it is secured against slipping out of the stomach (10) of its end (12') by a portion (18) of the catheter (12) assuming a spiral configuration in the interior of the stomach and resting on the stomach wall upon withdrawal of a trocar.

3 Claims, 3 Drawing Sheets

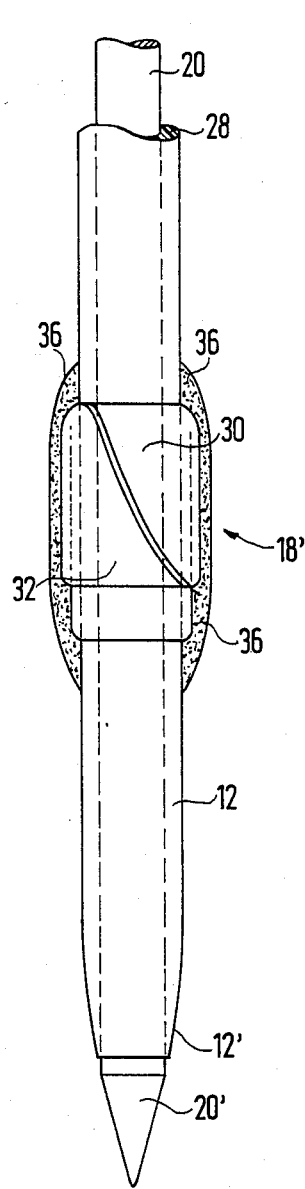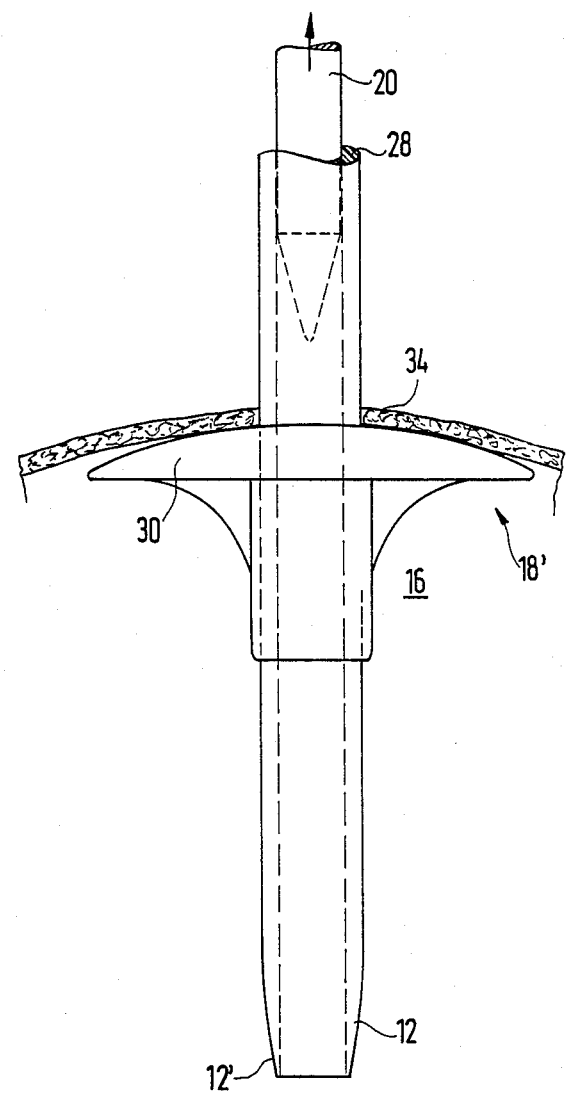

CATHETER FOR PERCUTANEOUS GASTROSTOMY

The instant invention relates to a catheter made of plastic material and used for percutaneous gastrostomy. It is inserted through the abdominal wall into the gastric lumen where it is located with respect to the stomach wall by a retaining means to be positioned in the gastric lumen.

Such a catheter is known from the journal "Die Medizinische Welt", 1985, 36, pp. 1297–1301.

In the percutaneous gastrostomy a patient is given "artificial alimentation" by feeding the nourishment directly into the stomach, bypassing the patient's organs of mastication and swallowing.

The so-called Witzel's operation is known for direct alimentation into the stomach. Yet it is a very complicated operation to form a gastric fistula in this manner. Therefore, recently it has been replaced more and more by percutaneous gastrostomy which is endoscopically controlled and which is being used apart from the known applications of a nutriment probe inserted through the nose and catheter jejunostomy.

In the percutaneous, endoscopically controlled gastrostomy (cf e.g. "Die Medizinische Welt", 1985, 36, pp. 1297–1301) a polyurethane catheter is used which is brought into position in the stomach with the aid of a gyroscope (endoscope) and by means of a filament introduced through the abdominal and stomach walls.

It requires expensive apparatus and quite some skill on the part of the surgeon to introduce the catheter in the percutaneous, endoscopically controlled gastrostomy according to the state of the art. First, a gastroscope is introduced into the stomach and air is injected for insufflation of the stomach. The protrusion of the mucous membrane of the stomach is made visible endoscopically within the range of the gleam of light by applying pressure with the finger on the abdominal wall. Thereupon, a cannula is advanced at a suitable place until it becomes visible in the gastric lumen through the gastroscope. Then a long guidance filament is threaded through the cannula into the gastric lumen where it is grasped by the biopsy forceps, to be pulled out of the patient's mouth. By means of this guidance filament the catheter then is pulled in the opposite direction through the patient's mouth into the stomach and out of the same through the abdominal wall.

Considerable difficulty in the percutaneous gastrostomy is caused by the fact that the catheter must be located reliably in the stomach. Difficulties arise especially when the catheter is slipped in because the stomach will contract again after the insufflation so that the catheter runs the risk of dropping out of the gastric wall with disastrous consequences. In the known endoscopically controlled gastrostomy, therefore, the catheter is furnished with a silicone disc which abuts against the gastric wall to warrant that the end of the catheter in the stomach will remain fixed in position with respect to the gastric wall and not slip out of the stomach.

It is, therefore, an object of the instant invention to provide a catheter of the generic kind in question which can be positioned rather easily in the stomach. It is also an object of the instant invention to make sure that there is no risk that the catheter will slip out of the stomach.

These and other objects which will become apparent as the description proceeds are met, in accordance with the invention, in a catheter of the kind specified initially in that the catheter comprises a portion serving as retaining means which is stretched out at least approximately rectilinearly during introduction of the catheter through the abdominal wall into the gastric lumen and assumes a curved shape upon insertion in the gastric lumen.

Instead of including the known silicone disc of the state of the art which, evidently, causes problems when being introduced into the stomach, the catheter according to the instant invention itself is of such design that it will locate itself firmly upon insertion into the gastric lumen by curving such that it can no longer slip out of the stomach.

In a preferred modification of the invention it is provided that the catheter will assume a straight, stretched configuration on a trocar slid into the catheter (whereby the catheter and the trocar inside the same are insertable through the abdominal and gastric walls into the gastric lumen) and, upon withdrawal of the trocar from the catheter, a portion of the catheter will automatically adopt a curved shape which engages the gastric wall from the inside so that the catheter is prevented from slipping out of the stomach.

In a preferred further development of the invention the portion mentioned of the catheter is curved spirally inside the stomach, the spiral configuration preferably including a so-called bearing portion facing toward the interior of the stomach. This design of the catheter with its spiral portion, including the bearing portion has the advantage that any tensile stress to which the catheter is subjected is distributed uniformly over a greater part of the curved portion.

In accordance with another variant of the invention at least one laid-in member made of a so-called memory alloy is embedded in the wall of the catheter. At one given temperature this laid-in member will keep a certain portion of the catheter stretched, while it will give the same a curved, for example spiral configuration at another given temperature.

It is also possible to combine the latter method of curving the predetermined catheter portion by means of a laid-in member made of a memory alloy with the method mentioned first according to which the catheter is preformed such that it will automatically adopt the curvilinear shape without any load when no trocar is inserted in the catheter.

In accordance with another variant of the invention the catheter is provided with a retaining means in that it comprises at least one structural component which is adapted to be opened like an umbrella. Initially this component adapted to be opened is in close engagement with the wall of the catheter, in other words, it does not project at right angles from the same. However, upon introduction of the catheter through the abdominal wall and the stomach wall into the gastric lumen this component unfolds automatically and comes to lie against the inner wall of the stomach so as to secure the end of the catheter in the stomach within the gastric lumen.

In a preferred modification of the invention the components at the catheter which are adapted to be opened like an umbrella at first are held in engagement with the catheter as the latter is introduced into the stomach by means of a cover which is adapted to be dissolved in the body, for instance a cover of gelatin.

Upon introduction into the gastric lumen the gelatin is dissolved so that the components which are spring-loaded can be unfolded and engage the inside of the gastric wall.

In accordance with another variant of the invention the components which are adapted to be opened also may be unfolded by a laid-in member made of a memory alloy. Details regarding the memory effect of alloys may be gathered, for instance, from the publication "Technische Mitteilung Krupp-Forschungsberichte", vol. 34 (1976) no. 1 (paper by F. Baumgart, J. Jorde, and H. Reiss).

The invention will be described further, by way of example, with reference to the accompanying drawings, in which FIGS. 1, 2, and 3 are diagrammatic presentations to illustrate the use of the catheter according to the invention;

FIG. 6 presents another embodiment of a catheter according to the invention; and FIG. 7 shows the catheter according to FIG. 6 in an unfolded condition.

Figure 1:
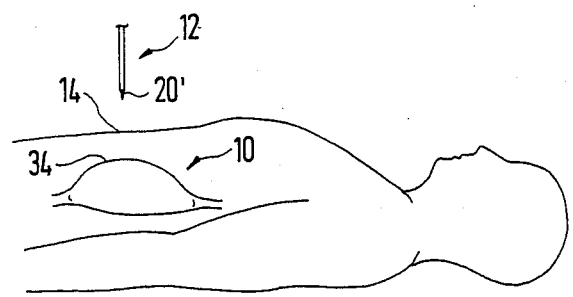
Figure 2:
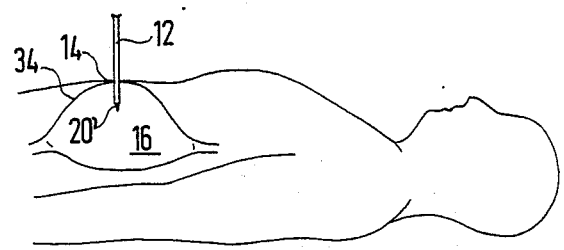
Figure 3:
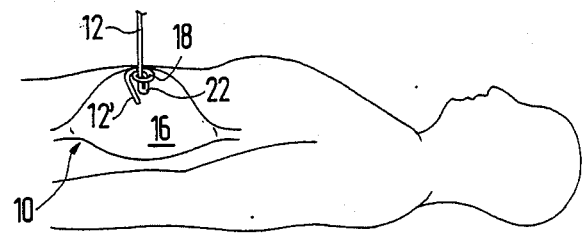

FIGS. 1, 2, and 3 show a patient who is prepared to receive nourishment by way of percutaneous gastrostomy. A catheter 12 is to be introduced directly through the abdominal wall 14 into the patient's stomach 10. Initially a trocar (cf. also FIGS. 4 and 6) is inserted in the catheter 12 made of plastic material. Hereby the catheter 12 is stretched to be rectilinear. By its tip 20' the trocar 20 seals the lower end of the catheter 12, and the trocar is introduced together with the catheter 12 through the abdominal wall 14 and the gastric wall 34 into the gastric lumen 16. The patient previously was administered bicarbonate of soda and ascorbic acid in order to cause the formation of $CO_2$ in the stomach. The gases thus forming inflate the stomach which will become insufflated as shown in FIG. 2, causing the gastric wall 34 to approach the abdominal wall 14. At a suitable place the trocar and the catheter 12 slipped over the same are pushed in through the abdominal wall 14 and the gastric wall 34 into the gastric lumen 16 (FIG. 2).

Subsequently the trocar 20 with its tip marked 20' is pulled out of the catheter 12. The catheter 12 is preformed of plastic material such that a portion 18 thereof immediately will curve spirally when the trocar has been pulled out, as shown in FIG. 3.

The curved portion 18 of catheter 12 engages the inside of the gastric wall 34 so that the end 12' of the catheter will be located in place in the gastric volume 16 and cannot slip out of the stomach 10.

Figure 4:
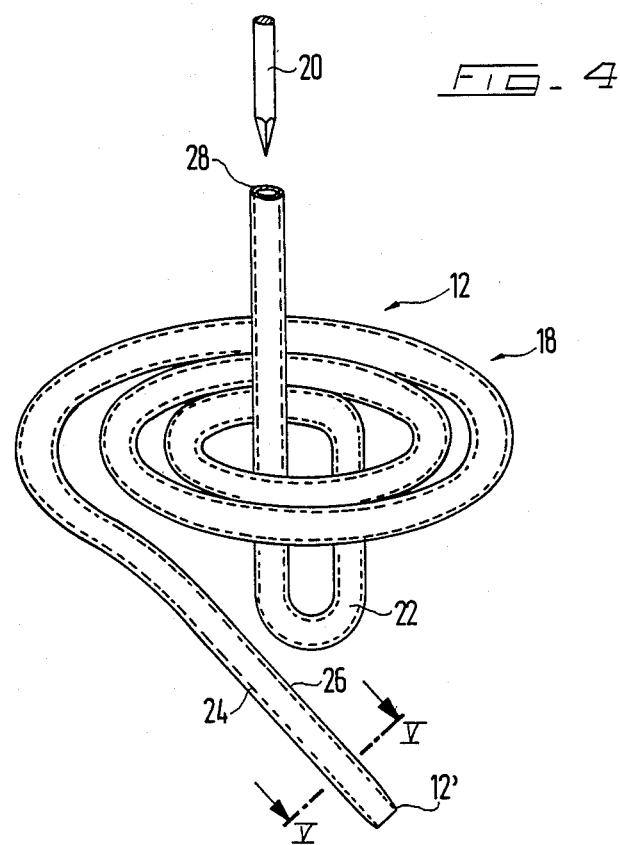
FIG. 4 shows part of a catheter in greater detail.
Figure 5:
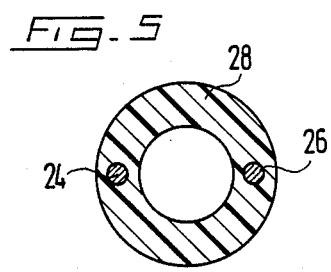
FIG. 5 is a section of the catheter in the area of the portion adapted to be curved.

The portion of catheter 12 held in the stomach 10 in accordance with FIG. 3 is shown on an enlarged scale in FIG. 4. As soon as the trocar 20 has been pulled out of the catheter 12, the catheter will assume the spiral shape shown in a predetermined portion 18. This automatic curvature of catheter 12, on the one hand, may be caused by the catheter itself being preformed spirally in portion 18 so that it will be stretched to be rectilinear only when the trocar 20 is inserted in the catheter, and/or by laid-in members 24, 26 provided in the wall 28 of the catheter 12 and winding into spiral shape in portion 18 when the trocar has been pulled out. To this end the laid-in members 24, 26 are made of a memory alloy. Therefore, at regular room temperature they will be substantially rectilinear and of stretched configuration, whereas they will assume the spiral configuration shown in FIG. 4 in the desired portion 18 of the catheter at body temperature (37° C.).

As shown in FIGS. 3 and 4, the spiral portion 18 of catheter 12 is provided with a so-called bearing portion 22 directed towards the interior of the stomach. This bearing portion guarantees that upon occurrence of tensile forces acting on the catheter 12, the pressures of the inside gastric wall will be distributed at least to one winding of the spiral portion 18 so that the end 12' of the catheter cannot slip out of the stomach 10.

Another embodiment of a catheter 12 having an end 12' which can be located reliably in the stomach 10 is shown in FIGS. 6 and 7. This catheter 12 is introduced by means of a trocar 20 in the same way as explained above with reference to FIGS. 1 to 3. The automatic curvature of the catheter 12 by bias of the material or of a laid-in member made of a memory alloy is substituted in the embodiment according to FIGS. 6 and 7 by an arrangement of structural elements or components 30, 32 which are adapted to be opened like an umbrella in the stomach. At first, as shown in FIG. 6, the components 30, 32 adapted to be opened are held in flush engagement against the catheter 12. To this end they are surrounded by a gelatin cover 36 introduced into the gastric lumen 16 together with the catheter 12 and made of alcohols exhibiting physiological tolerance. In the gastric lumen the gelatin cover 36 is dissolved so that the components 30, 32 which are adapted to be opened become unfolded under spring load, assuming the position shown in FIG. 7. It is obvious that the components 30, 32 adapted to be opened are connected firmly to the catheter 12. As shown in FIG. 7, the unfolded components 30, 32 enter into engagement like an umbrella with the inside of the gastric wall 34 so that the end 12' of the catheter 12 cannot slip out of the stomach 10.

The spring bias required for opening the components 30, 32 likewise may be provided by a laid-in member made of a memory alloy.

At the outside of the abdominal wall 14 the catheter may be secured with a conventional plastic disc which engages the abdominal wall from the outside.

For removal from the stomach, the catheter having the curved design of the embodiment shown in FIGS. 1 to 4 simply may be rotated. In the case of the other embodiment shown in FIGS. 6 and 7 the resilient forces are dimensioned such that the components, when opened, will yield to extremely strong pulling at the catheter.

What is claimed is:

1. A catheter of plastic material for percutaneous gastrostomy inserted through an abdominal wall into a gastric lumen and located there with respect to a stomach wall by a retaining means to be positioned in the gastric lumen, wherein the catheter comprises a portion serving as remaining means which is stretched out at least approximately rectinlinearly during the introduction of the catheter through the abdominal wall into the gastric lumen, and after insertion in the gastric lumen said portion of the catheter assumes a spirally curved configuration including a bearing portion facing toward the interior of said gastric lumen such that any tensile stress to which the catheter is subjected, is distributed uniformly over a great part of the curved portion, and a free end of the catheter is directed toward the interior of said gastric lumen, wherein said portion of the catheter assumes a spirallly curved configuration such that a plane of the spiral is perpendicular to the direction of the bearing portion and a section of the catheter which passes the stomach wall.

2. A catheter of plastic material for percutaneous gastrostomy inserted through an abdominal wall into a gastric lumen and located there with respect to a stomach wall by a retaining means to be positioned in the gastric lumen, wherein the catheter comprises a portion serving as retaining means which is stretched out at least approximately rectinlinearly during introduction of the catheter through the abdominal wall into the gastric lumen and assumes a curved shape upon insertion in the gastric lumen, and after insertion in the gastric lumen, said portion of the catheter assumes a spirally curved configuration including a bearing portion facing toward the interior of said gastric lumen such that any tensile stress to which the catheter is subjected, is distributed uniformly over a great part of the curved portion, and a free end of the catheter is directed toward the interior of said gastric lumen, wherein the wall of the catheter contains at least one laid-in member made of a memory alloy which is embedded in the wall and leaves said portion of the catheter stretched at one given temperature, where it will adopt the spirally curved configuration at another given temperature.

3. The catheter as in claim 2, wherein two laid-in members of memory alloy are embedded diametrically opposite each other in the catheter wall.

* * * * *